(12) United States Patent
Hirao

(10) Patent No.: US 8,906,638 B2
(45) Date of Patent: Dec. 9, 2014

(54) METHOD FOR QUANTIFICATION OF REMNANT-LIKE LIPOPROTEIN CHOLESTEROL AND KIT FOR SAME

(75) Inventor: Yuhko Hirao, Gosen (JP)

(73) Assignee: Denka Seiken Co., Ltd., Tokyo (JP)

( * ) Notice: Subject to any disclaimer, the term of this patent is extended or adjusted under 35 U.S.C. 154(b) by 0 days.

(21) Appl. No.: 13/884,475

(22) PCT Filed: Nov. 9, 2011

(86) PCT No.: PCT/JP2011/075837
§ 371 (c)(1),
(2), (4) Date: May 9, 2013

(87) PCT Pub. No.: WO2012/063866
PCT Pub. Date: May 18, 2012

(65) Prior Publication Data
US 2013/0230873 A1 Sep. 5, 2013

(30) Foreign Application Priority Data

Nov. 10, 2010 (JP) .................................. 2010-251511

(51) Int. Cl.
*C12Q 1/60* (2006.01)
*G01N 33/92* (2006.01)
*C12Q 1/44* (2006.01)

(52) U.S. Cl.
CPC ...... *C12Q 1/60* (2013.01); *G01N 33/92* (2013.01); *C12Q 1/44* (2013.01); *G01N 2333/918* (2013.01)
USPC .............................................. 435/11; 436/71

(58) Field of Classification Search
None
See application file for complete search history.

(56) References Cited

U.S. PATENT DOCUMENTS

| | | | |
|---|---|---|---|
| 2008/0124748 A1* | 5/2008 | Matsui et al. ................... | 435/11 |
| 2009/0170139 A1* | 7/2009 | Mishima et al. ................ | 435/11 |

FOREIGN PATENT DOCUMENTS

| | | | |
|---|---|---|---|
| EP | 1132482 A2 | 9/2001 | |
| EP | 1477570 A1 | 11/2004 | |
| EP | 1818412 A1 | 8/2007 | |
| EP | 1959021 A1 | 8/2008 | |
| EP | 1975244 A1 | 10/2008 | |
| EP | 2634261 A1 * | 4/2013 | ............... C12Q 1/60 |
| JP | 2001-231597 A | 8/2001 | |

OTHER PUBLICATIONS

Asahi Kasei Pharma Corporation, "Cholesterol esterase (CEN) from *Pseudomonas* sp." data sheet, available from the company's webpage, 2011.*
International Search Report dated Jan. 17, 2012 for International Application No. PCT/JP2011/075837.
Nakajima et al., "III Kyoketsusei Shinshikkan no Kentai Kensa 2, Domyaku Kokasho no Shindan Marker Remnant Lipoprotein Cholesterol," Medical Technology, 2004, vol. 32, No. 13, pp. 1462-1464.

\* cited by examiner

*Primary Examiner* — Ruth Davis
*Assistant Examiner* — Emily Cordas
(74) *Attorney, Agent, or Firm* — Birch, Stewart, Kolasch & Birch, LLP

(57) ABSTRACT

A method for quantifying remnant-like lipoprotein cholesterol in a sample simply and accurately without requiring separation operations, and a kit therefor are disclosed. A method for quantifying cholesterol in a remnant-like lipoprotein in a sample containing different lipoproteins including the remnant-like lipoprotein comprises a step (1) of erasing cholesterol in lipoproteins other than the remnant-like lipoprotein; and a step (2) of quantifying cholesterol in the remaining remnant-like lipoprotein. The step (1) is carried out under an action of a cholesterol esterase having a molecular weight of more than 40 kDa and not having a subunit having a molecular weight of not more than 40 kDa; and the step (2) is carried out under an action of a cholesterol esterase having a molecular weight of not more than 40 kDa or a cholesterol esterase having a subunit having a molecular weight of not more than 40 kDa.

5 Claims, 2 Drawing Sheets

METHOD FOR QUANTIFICATION OF REMNANT-LIKE LIPOPROTEIN CHOLESTEROL AND KIT FOR SAME

TECHNICAL FIELD

The present invention relates to a method for quantifying cholesterol in remnant-like lipoprotein (RLP) and a kit therefor.

BACKGROUND ART

Lipoproteins contained in blood are classified into chylomicron, very low density lipoprotein (VLDL), intermediate-density lipoprotein (IDL), low density lipoprotein (LDL) and high density lipoprotein (HDL) depending on the difference in density by ultracentrifugation. These lipoproteins are known to have varying contents of lipids such as triglyceride and cholesterol, and proteins. Each lipoprotein has a different function in vivo.

RLP is an intermediary metabolite of the lipoproteins such as chylomicron and VLDL, having a large content of triglyceride. Although RLP is usually metabolized rapidly and removed from blood, when some metabolic disorders occurred, the RLP remains and accumulates in the blood. The RLP is likely to deposit on the artery wall, and is considered to be one of arteriosclerosis-inducing lipoproteins.

As a method for quantifying cholesterol in RLP, a method is known wherein RLP is separated from serum by using affinity gel containing anti-apo A-I monoclonal antibody and anti-apo B-100 monoclonal antibody, and cholesterol contained in the separated RLP is measured, and a reagent therefor is commercially available.

On the other hand, as a method for quantifying RLP cholesterol without requiring separation operations, a method has been recently reported wherein a sample is treated with a cholesterol esterase, cholesterol oxidase or cholesterol dehydrogenase, and phospholipase (Patent Literature 1). In addition to this, a method using two kinds of surfactants (Patent Literature 2), a method using a cholesterol esterase wherein the ratio of lipoprotein lipase activity and cholesterol esterase activity is from 12 to 7000 (Patent Literature 3) and a method using a surfactant having a benzenesulfonic acid structure or a polyacrylic acid surfactant (Patent Literature 4) have been reported.

PRIOR ART REFERENCES

Patent Literatures

Patent Literature 1: Japanese Patent No. 4456715
Patent Literature 2: WO 2007/066760
Patent Literature 3: WO 2006/057377
Patent Literature 4: WO 2007/083523

DISCLOSURE OF THE INVENTION

Problems to be Solved by the Invention

An object of the present invention is to provide a method for quantifying RLP cholesterol in a sample simply and accurately without requiring separation operations, and to provide a kit therefor.

Means for Solving the Problems

The present inventors found in enzymatically measuring cholesterol in a sample containing various kinds of lipoproteins that, in cases where the test sample is treated with a cholesterol esterase having a molecular weight of more than 40 kDa and not having a subunit having a molecular weight of not more than 40 kDa, lipoproteins other than RLP are reacted with the cholesterol esterase; and in cases where the test sample is treated with a cholesterol esterase having a molecular weight of not more than 40 kDa or a cholesterol esterase having a subunit having a molecular weight of not more than 40 kDa, all the lipoproteins including RLP are reacted with the cholesterol esterase. By using the finding, the present inventors inferred that cholesterol in RLP can be quantified simply without carrying out separation operations, thereby completing the present invention.

That is, the present invention is as follows:

[1] A method for quantifying remnant-like lipoprotein cholesterol in a sample containing different lipoproteins including remnant-like lipoprotein, said method comprising:
a step (1) of erasing cholesterol in lipoproteins other than the remnant-like lipoprotein; and
a step (2) of quantifying cholesterol in the remaining remnant-like lipoprotein, wherein said step (1) is carried out under an action of a cholesterol esterase having a molecular weight of more than 40 kDa and not having a subunit having a molecular weight of not more than 40 kDa; and said step (2) is carried out under an action of a cholesterol esterase having a molecular weight of not more than 40 kDa or a cholesterol esterase having a subunit having a molecular weight of not more than 40 kDa.

[2] The method according to [1], wherein said step (1) comprises treating said sample with said cholesterol esterase and a cholesterol oxidase, and erasing generated hydrogen peroxide, and said step (2) comprises treating said sample with said cholesterol esterase and a cholesterol oxidase, and quantifying generated hydrogen peroxide.

[3] The method according to [1] or [2], wherein said step (1) and said step (2) are carried out in the presence of a nonionic surfactant.

[4] The method according to any one of [1] to [3], wherein said nonionic surfactant used in said step (1) and said step (2) is at least one selected from the group consisting of a polyoxyethylene derivative having an HLB value of 11 to 13, polyoxyethylene alkyl ether, polyoxyalkylene alkyl ether and polyoxyethylene alkyl phenyl ether.

[5] The method according to any one of [1] to [4], wherein said step (1) further comprises treating said sample with a phospholipase.

[6] A kit for quantifying remnant-like lipoprotein cholesterol, said kit comprising at least the following two reagent compositions:
(i) a reagent composition for erasing and transferring cholesterol in lipoproteins other than remnant-like lipoprotein in a test sample to the outside of reaction system, the composition comprising a cholesterol esterase having a molecular weight of more than 40 kDa and not having a subunit having a molecular weight of not more than 40 kDa;
(ii) a reagent composition for quantifying cholesterol in the remnant-like lipoprotein, the composition comprising a cholesterol esterase having a molecular weight of not more than 40 kDa or a cholesterol esterase having a subunit having a molecular weight of not more than 40 kDa.

[7] The kit according to [6], wherein at least said reagent composition (i) comprises a cholesterol oxidase.

[8] The kit according to [6] or [7], wherein said reagent compositions (i) and (ii) comprise at least one nonionic surfactant selected from the group consisting of a polyoxyethylene derivative having an HLB value of 11 to 13, polyoxyethylene alkyl ether and polyoxyethylene alkyl phenyl ether.

The kit according to any one of [6] to [8], wherein said reagent composition (i) further comprises a phospholipase.

Effect of the Invention

By the present invention, a novel method capable of quantifying RLP cholesterol in a sample simply and accurately without requiring separation operations, and a kit therefor were provided.

MODE FOR CARRYING OUT THE INVENTION

Figure 1:
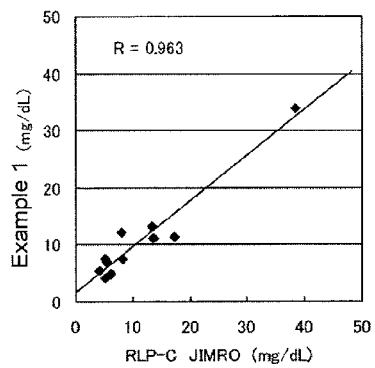
FIG. 1 shows the correlation between the quantification results of cholesterol in RLP by the method of the present invention described in Example 1 below and the quantification results by a known method using anti-RLP monoclonal antibody.

Examples of cholesterol contained in lipoproteins include ester type cholesterol (cholesterol ester) and free cholesterol. In this specification, the term "cholesterol" includes both of these unless otherwise specified The RLP to be quantified by the method of the present invention means lipoproteins of the total of chylomicron remnant and VLDL remnant.

Although the sample subjected to the method of the present invention is not restricted as long as it contains different lipoproteins including remnant-like lipoprotein, it is usually body fluids such as blood (including whole blood, sera and plasma) and dilutions thereof.

In the step (1) of the present invention, cholesterol in lipoproteins other than RLP is selectively erased. The term "erase" herein means to decompose the cholesterol and to make the decomposed products undetectable in the subsequent step (2). Examples of methods for erasing cholesterol selectively contained in lipoproteins other than RLP include, for example, a method in which a test sample is treated with a cholesterol oxidase and a specific cholesterol esterase (described below), and generated hydrogen peroxide is removed. Examples of methods for removing hydrogen peroxide include a method in which the hydrogen peroxide is decomposed to water and oxygen by catalase; and a method in which a hydrogen donor compound which reacts with hydrogen peroxide to yield a colorless quinone, is converted to the colorless quinone by peroxidase, although the methods for removing hydrogen peroxide are not restricted to these methods.

The methods for erasing cholesterol selectively in the specific lipoprotein in the first step are widely employed for a method for quantifying LDL cholesterol (for example, WO 98/47005, U.S. Pat. No. 6,194,164 B1 and the like) and a method for quantifying HDL cholesterol (for example, WO 98/26090, U.S. Pat. No. 6,479,249 B2 and the like), and are well-known (these patent publications are hereby incorporated by reference). The step (1) of the present invention can be carried out by such well-known methods except that the specific cholesterol esterase described below is used. The term "erase" herein means to decompose the cholesterol and to make the decomposed products undetectable in the subsequent second step. Examples of the method for erasing lipoproteins other than RLP, that is cholesterol contained in HDL, LDL, VLDL, CM and the like, include the following methods. That is, in the first method, a test sample is treated with a cholesterol esterase and a cholesterol oxidase to remove generated hydrogen peroxide. By the action of the cholesterol esterase, the ester type cholesterol in the lipoproteins is hydrolyzed to yield free cholesterol and fatty acids. Then, the generated free cholesterol and free cholesterol inherently existing in the lipoproteins are oxidized under an action of a cholesterol oxidase to yield cholestenone and hydrogen peroxide. The thus generated hydrogen peroxide is removed. Examples of the method for removing hydrogen peroxide include a method in which the hydrogen peroxide is decomposed to water and oxygen by catalase; and a method in which a phenol-based or aniline-based hydrogen donor compound, such as DAOS (N-ethyl-N-(2-hydroxysulfopropyl)-3,5-dimethioxyaniline), which reacts with hydrogen peroxide to yield a colorless quinone, is reacted with the hydrogen peroxide to convert the hydrogen peroxide to the colorless quinone under an action of peroxidase, although the methods for removing hydrogen peroxide are not restricted to these methods.

Although a phospholipase may or may not be used in the step (1) of the present invention, a suitable phospholipase can promote to erase cholesterol in lipoproteins other than RLP. Preferred examples of the phospholipase include phospholipase C (PLC), sphingomyelinase (SPC), phosphatidyl inositol-specific phospholipase C (PI-PLC, all of the above-described are produced by ASAHI KASEI PHARMA), sphingomyelinase (originated from *Bacillus cereus*), sphingomyelinase (originated from *Staphylococcus aureus*), phosphatidyl inositol-specific phospholipase C (originated from *Bacillus cereus*, all of the above-described are produced by SIGMA), but the phospholipase is not restricted thereto.

In the following step (2), a specific cholesterol esterase described below is added to the reaction product in the step (1), and the cholesterol in RLP is enzymatically quantified. The method for enzymatically quantifying cholesterol per se is well-known in the art. Examples of such a method include a method in which cholesterol is treated with a cholesterol oxidase and a cholesterol esterase, generated hydrogen peroxide is converted to a quinone pigment by a peroxidase, hydrogen donor and hydrogen acceptor, and absorbance of the pigment is measured to quantify the cholesterol. Such methods are widely used and well-known methods, and are described also in the above-described WO 98/47005 and WO 98/26090.

In cases where it is necessary to decompose the hydrogen peroxide generated in the step (1) with catalase, and to inhibit the catalase in the step (2), the catalase is inhibited with a catalase inhibitor such as sodium azide in the step (2).

A nonionic surfactant is preferably made to coexist in the step (1) and the step (2) of the present invention. Preferable surfactant can promote an enzyme reaction in each step. Examples of the preferable surfactant include a polyoxyethylene derivative having an HLB value of 11 to 13, polyoxyethylene alkyl ether, polyoxyalkylene alkyl ether and polyoxyethylene alkyl phenyl ether. Specific examples of the surfactant include Emulgen A-60, Emulgen 707, Emulgen 709 and Emulgen 909 (all of the above-described are produced by KAO CORPORATION); and Blaunon DSP-9 and Blaunon DSP-12.5 (both are produced by AOKI OIL).

The surfactant made to coexist in the step (1) and the step (2) may be the same or different. The concentration of the surfactant in reaction solution is preferably from 0.05% to 5%, and more preferably from 0.1% to 1%.

The cholesterol oxidase used in the present invention is not restricted as long as it is an enzyme having an ability to oxidize cholesterol to generate hydrogen peroxide, and examples of the cholesterol oxidase include a cholesterol esterase originated from animals or microbes. The cholesterol oxidase may be produced by genetic manipulations, and may be chemically modified or not.

Although the amount of each enzyme used in the present invention varies depending on the kinds of the enzyme and is not restricted, it is usually from 0.001 to 2000 U/mL, and preferably from 0.1 to 1000 U/mL.

The hydrogen donor used in the present invention is preferably an aniline derivative. Examples of the aniline derivative include N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(3-sulfopropyl)-3-methylaniline (TOPS), N-(2-hydroxy-3-sulfopropyl)-3,5-dimethoxyaniline (HDAOS), N-(3-sulfopropyl)aniline (HALPS) and N-(3-sulfopropyl)-3-methoxy-5-aniline (HMMPS).

As the hydrogen acceptor, 4-aminoantipyrine, methyl benzothiazolone hydrazone and the like may be used.

Each step of the present invention is preferably carried out at pH 5 to 10, and more preferably at pH 6 to 8.

Each step is preferably carried out at a reaction temperature of 2° C. to 45° C., and more preferably of 25° C. to 40° C. The reaction time in each step is preferably from 1 to 10 minutes, and more preferably from 3 to 7 minutes.

The most characteristic feature of the present invention resides in that a different cholesterol esterase is used between the step (1) and the step (2). As mentioned above, the present inventors found in enzymatically measuring cholesterol in a test sample containing various kinds of lipoproteins that, in cases where the test sample is treated with a cholesterol esterase having a molecular weight of more than 40 kDa and not having a subunit having a molecular weight of not more than 40 kDa (hereinafter referred to as "high-molecular-weight cholesterol esterase" for convenience), lipoproteins other than RLP are reacted with the cholesterol esterase; and in cases where the test sample is treated with a cholesterol esterase having a molecular weight of not more than 40 kDa or a cholesterol esterase having a subunit having a molecular weight of not more than 40 kDa (hereinafter referred to as "low-molecular-weight cholesterol esterase" for convenience), all the lipoproteins including RLP are reacted with the cholesterol esterase. Although not bound by a theory, it is thought that a triglyceride exists abundantly with an ester type cholesterol in the inside of RLP, and since the triglyceride provides steric hindrance, the high-molecular-weight cholesterol esterase of large size cannot access to and react with the ester type cholesterol in the inside of particles.

By using the above-described findings, in the method of the present invention, the step (1) is carried out under an action of a high-molecular-weight cholesterol esterase and the step (2) is carried out under an action of a low-molecular-weight cholesterol esterase. As mentioned above, since the generated cholesterol (cholesterol originated from lipoproteins other than RLP) is erased in the step (1), RLP cholesterol alone is quantified in the step (2).

The molecular weight of the cholesterol esterase and the subunit thereof are measured by the conventional SDS-polyacrylamide electrophoresis (SDS-PAGE). As is well-known, since the SDS-PAGE is an electrophoresis performed under reduced condition, in cases where the cholesterol esterase is constituted by a plurality of subunit, the cholesterol esterase is dissociated to the subunits, so that the molecular weight of each subunit is measured. On the other hand, in cases where the cholesterol esterase does not have a subunit, the molecular weight of the cholesterol esterase is measured.

Commercially available examples of the high-molecular-weight cholesterol esterase include cholesterol esterase (CEBP-M produced by ASAHI KASEI PHARMA, molecular weight: 62 kDa), cholesterol esterase (CHE-XE produced by KIKKOMAN, molecular weight: 54 kDa) and the like.

Commercially available examples of the low-molecular-weight cholesterol esterase include cholesterol esterase (CEN produced by ASAHI KASEI PHARMA, molecular weight: 29.5 kDa), cholesterol esterase "Amano" 2 (CHE2 produced by AMANO ENZYME, molecular weight: 30 kDa), cholesterol esterase "Amano" 3 (CHE3 produced by AMANO ENZYME, molecular weight: 30 kDa) and the like.

In carrying out the method for quantification of the present invention, reagents to be used may be divided into a plurality of reagent compositions. As the reagents in the present invention, for example, two reagent compositions can be prepared which are a reagent composition for carrying out the step of erasing cholesterol in lipoproteins other than RLP (i.e. step (1)), and a reagent composition for carrying out the step of measuring cholesterol in RLP (i.e. step (2)).

The reagent composition for carrying out the step (1) contains at least a high-molecular-weight cholesterol esterase. The reagent composition may further contain the above-described surfactant, cholesterol oxidase, hydrogen donor such as an aniline derivative, catalase for erasing hydrogen peroxide and the like.

The reagent composition for carrying out the step (2) contains at least a low-molecular-weight cholesterol esterase. The reagent composition may further contain a surfactant, hydrogen acceptor such as 4-aminoantipyrine, peroxidase and the like.

A monovalent cation (for example, a monovalent metal ion), a divalent cation (for example, a divalent metal ion) or a salt thereof, a polyanion (for example, heparin, dextran sulfate, phosphotungstate), and serum albumin may be added to the reagent composition for carrying out the step (1) and the reagent composition for carrying out the step (2) as required. The pH of each reagent composition is in the vicinity of neutral, and for example, pH 5 to 9, preferably pH 6 to 8, and a buffer solution may be added to adjust the pH of the reagent composition.

In order to quantify cholesterol in RLP according to the method of the present invention, the method may be carried out by adding the reagent composition for carrying out the step (1) to a test sample to allow the reaction, then adding the reagent composition for carrying out the step (2) to the resultant to allow the reaction, and measuring absorbance. As mentioned above, the step (1) and the step (2) can be carried out by usual methods except that the above-described specific cholesterol esterase is used respectively.

The present invention will now be described concretely by way of Examples. However, the present invention is not restricted to the Examples below.

EXAMPLES

Example 1

Reagent Composition A for carrying out the step (1) (the reagent composition for carrying out the step (1) is referred to as "Reagent Composition A" also in Example 2 or later) and Reagent Composition B for carrying out the step (2) (the reagent composition for carrying out the step (2) is referred to as "Reagent Composition B" also in Example 2 or later) were prepared in the following way:

Reagent Composition A

| | |
|---|---|
| PIPES buffer solution, pH 6.8 | 50 mmol/L |
| Cholesterol esterase [CEBP-M produced by ASAHI KASEI PHARMA] | 5 U/mL |
| Cholesterol oxidase | 2.5 U/mL |
| Catalase | 1000 U/mL |
| TOOS | 2.0 mmol/L |
| Emulgen A-60 (Trade Name) | 0.1% (w/v) |

Reagent Composition B

| | |
|---|---|
| PIPES buffer solution, pH 6.8 | 50 mmol/L |
| Cholesterol esterase [CEN produced by ASAHI KASEI PHARMA] | 4 U/mL |
| 4-Aminoantipyrine | 4.0 mmol/L |
| Peroxidase | 20 units/mL |
| Sodium azide | 0.05% (w/v) |
| Emulgen A-60 (Trade Name) | 0.1% (w/v) |

To 5 µL of a serum sample, 270 µL of the Reagent Composition A was added, and after reaction at 37° C. for 5 minutes, 90 µL of the Reagent Composition B was added to the resultant to allow the reaction for 5 minutes, and the absorbance was measured at a primary wavelength of 600 nm and a secondary wavelength of 700 nm.

For comparison, the concentrations of cholesterol in RLP were measured with RLP-cholesterol "JIMRO" II (Trade Name) produced by OTSUKA PHARMACEUTICAL containing anti-RLP monoclonal antibodies. The result is shown in FIG. 1.

As shown in FIG. 1, a good correlation was observed between the method of this Example and the method using RLP-cholesterol "JIMRO" II (Trade Name) which is a reagent for measuring RLP cholesterol.

Example 2

The Reagent Composition A and the Reagent Composition B were prepared in the following way:

Reagent Composition A

| | |
|---|---|
| PIPES buffer solution, pH 6.8 | 50 mmol/L |
| Cholesterol esterase [CEBP-M produced by ASAHI KASEI PHARMA] | 5 U/mL |
| Cholesterol oxidase | 2.5 U/mL |
| Sphingomyelinase [SPC produced by ASAHI KASEI PHARMA] | 2.5 U/mL |
| Catalase | 1000 U/mL |
| TOOS | 2.0 mmol/L |
| Emulgen A-60 (Trade Name) | 0.1% (w/v) |

Reagent Composition B

| | |
|---|---|
| PIPES buffer solution, pH 6.8 | 50 mmol/L |
| Cholesterol esterase [CEN produced by ASAHI KASEI PHARMA] | 4 U/mL |
| 4-Aminoantipyrine | 4.0 mmol/L |
| Peroxidase | 20 units/mL |
| Sodium azide | 0.05% (w/v) |
| Emulgen A-60 (Trade Name) | 0.1% (w/v) |

The measurement was carried out in the same manner as in Example 1, and the measurement result was compared with the value obtained by using RLP-cholesterol "JIMRO" II (Trade Name). The result is shown in FIG. 2.

Figure 2:
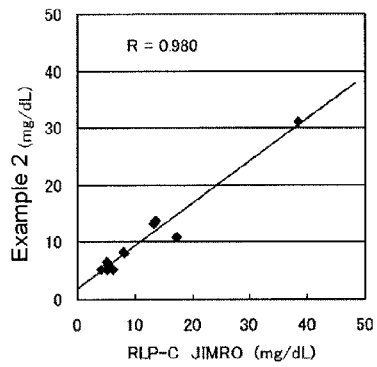
FIG. 2 shows the correlation between the quantification results of cholesterol in RLP by the method of the present invention described in Example 2 below and the quantification results by a known method using anti-RLP monoclonal antibody.

As shown in FIG. 2, a good correlation was observed between the method of this Example and the method using RLP-cholesterol "JIMRO" II (Trade Name) which is a reagent for measuring RLP cholesterol.

Example 3

The Reagent Composition A and the Reagent Composition B were prepared in the following way:

Reagent Composition A

| | |
|---|---|
| PIPES buffer solution, pH 6.8 | 50 mmol/L |
| Cholesterol esterase [CEBP-M produced by ASAHI KASEI PHARMA] | 5 U/mL |
| Cholesterol oxidase | 2.5 U/mL |
| Sphingomyelinase [SPC produced by ASAHI KASEI PHARMA] | 2.5 U/mL |
| Catalase | 1000 U/mL |
| TOOS | 2.0 mmol/L |
| Emulgen A-60 (Trade Name) | 0.1% (w/v) |

Reagent Composition B

| | |
|---|---|
| PIPES buffer solution, pH 6.8 | 50 mmol/L |
| Cholesterol esterase [CEN produced by ASAHI KASEI PHARMA] | 4 U/mL |
| 4-Aminoantipyrine | 4.0 mmol/L |
| Peroxidase | 20 units/mL |
| Sodium azide | 0.05% (w/v) |
| Emulgen 709 (Trade Name) | 0.1% (w/v) |

The measurement was carried out in the same manner as in Example 1, and the measurement result was compared with the value obtained by using RLP-cholesterol "JIMRO" II (Trade Name). The result is shown in FIG. 3.

Figure 3:
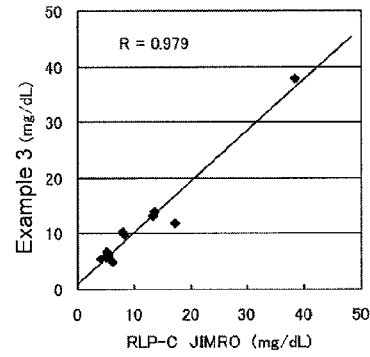
FIG. 3 shows the correlation between the quantification results of cholesterol in RLP by the method of the present invention described in Example 3 below and the quantification results by a known method using anti-RLP monoclonal antibody.

As shown in FIG. 3, a good correlation was observed between the method of this Example and the method using RLP-cholesterol "JIMRO" II (Trade Name) which is a reagent for measuring RLP cholesterol.

Example 4

The Reagent Composition A and the Reagent Composition B were prepared in the following way:

Reagent Composition A

| | |
|---|---|
| PIPES buffer solution, pH 6.8 | 50 mmol/L |
| Cholesterol esterase [CEBP-M produced by ASAHI KASEI PHARMA] | 5 U/mL |
| Cholesterol oxidase | 2.5 U/mL |
| Sphingomyelinase [SPC produced by ASAHI KASEI PHARMA] | 2.5 U/mL |
| Catalase | 1000 U/mL |
| TOOS | 2.0 mmol/L |
| Blaunon DSP-12.5 (Trade Name) | 0.1% (w/v) |

Reagent Composition B

| | |
|---|---|
| PIPES buffer solution, pH 6.8 | 50 mmol/L |
| Cholesterol esterase [CEN produced by ASAHI KASEI PHARMA] | 4 U/mL |
| 4-Aminoantipyrine | 4.0 mmol/L |
| Peroxidase | 20 units/mL |
| Sodium azide | 0.05% (w/v) |
| Emulgen A-60 (Trade Name) | 0.1% (w/v) |

The measurement was carried out in the same manner as in Example 1, and the measurement result was compared with the value obtained by using RLP-cholesterol "JIMRO" II (Trade Name). The result is shown in FIG. 4.

Figure 4:
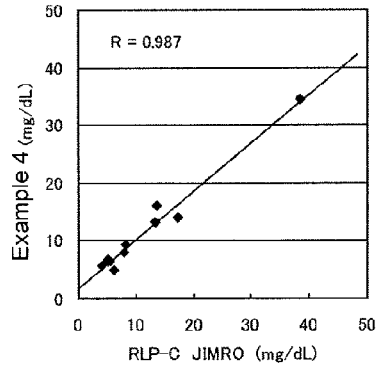
FIG. 4 shows the correlation between the quantification results of cholesterol in RLP by the method of the present invention described in Example 4 below and the quantification results by a known method using anti-RLP monoclonal antibody.

As shown in FIG. 4, a good correlation was observed between the method of this Example and the method using RLP-cholesterol "JIMRO" II (Trade Name) which is a reagent for measuring RLP cholesterol.

Example 5

The Reagent Composition A and the Reagent Composition B were prepared in the following way:

Reagent Composition A

| | |
|---|---|
| PIPES buffer solution, pH 6.8 | 50 mmol/L |
| Cholesterol esterase [CEBP-M produced by ASAHI KASEI PHARMA] | 5 U/mL |
| Cholesterol oxidase | 2.5 U/mL |
| Sphingomyelinase [SPC produced by ASAHI KASEI PHARMA] | 2.5 U/mL |
| Catalase | 1000 U/mL |
| TOOS | 2.0 mmol/L |
| Emulgen A-60 (Trade Name) | 0.1% (w/v) |
| Bovine serum albumin | 0.1% (w/v) |

Reagent Composition B

| | |
|---|---|
| PIPES buffer solution, pH 6.8 | 50 mmol/L |
| Cholesterol esterase [CEN produced by ASAHI KASEI PHARMA] | 4 U/mL |
| 4-Aminoantipyrine | 4.0 mmol/L |
| Peroxidase | 20 units/mL |
| Sodium azide | 0.05% (w/v) |
| Emulgen A-60 (Trade Name) | 0.1% (w/v) |

The measurement was carried out in the same manner as in Example 1, and the measurement result was compared with the value obtained by using RLP-cholesterol "JIMRO" II (Trade Name). The result is shown in FIG. 5.

Figure 5:
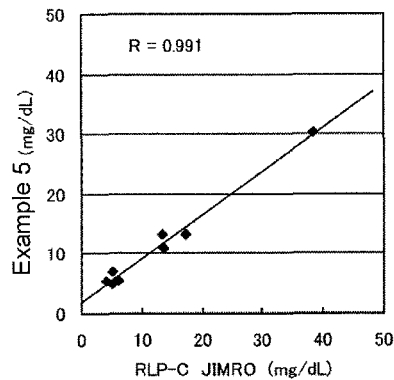
FIG. 5 shows the correlation between the quantification results of cholesterol in RLP by the method of the present invention described in Example 5 below and the quantification results by a known method using anti-RLP monoclonal antibody.

As shown in FIG. 5, a good correlation was observed between the method of this Example and the method using RLP-cholesterol "JIMRO" II (Trade Name) which is a reagent for measuring RLP cholesterol.

Example 6

The Reagent Composition A and the Reagent Composition B were prepared in the following way:

Reagent Composition A

| | |
|---|---|
| PIPES buffer solution, pH 6.8 | 50 mmol/L |
| Cholesterol esterase [CHE-XE produced by KIKKOMAN] | 5 U/mL |
| Cholesterol oxidase | 2.5 U/mL |
| Sphingomyelinase [SPC produced by ASAHI KASEI PHARMA] | 2.5 U/mL |
| Catalase | 1000 U/mL |
| TOOS | 2.0 mmol/L |
| Emulgen A-60 (Trade Name) | 0.1% (w/v) |
| Bovine serum albumin | 0.1% (w/v) |

Reagent Composition B

| | |
|---|---|
| PIPES buffer solution, pH 6.8 | 50 mmol/L |
| Cholesterol esterase [CEN produced by ASAHI KASEI PHARMA] | 4 U/mL |
| 4-Aminoantipyrine | 4.0 mmol/L |
| Peroxidase | 20 units/mL |
| Sodium azide | 0.05% (w/v) |
| Emulgen 709 (Trade Name) | 0.1% (w/v) |

The measurement was carried out in the same manner as in Example 1, and the measurement result was compared with the value obtained by using RLP-cholesterol "JIMRO" II (Trade Name). The result is shown in FIG. 6.

Figure 6:
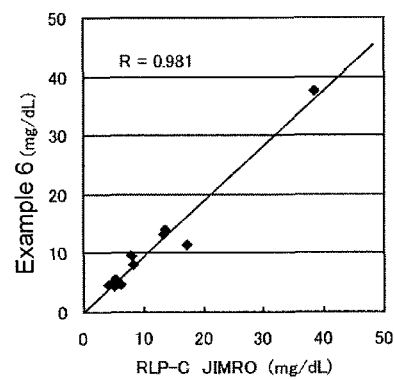
FIG. 6 shows the correlation between the quantification results of cholesterol in RLP by the method of the present invention described in Example 6 below and the quantification results by a known method using anti-RLP monoclonal antibody.

As shown in FIG. 6, a good correlation was observed between the method of this Example and the method using RLP-cholesterol "JIMRO" II (Trade Name) which is a reagent for measuring RLP cholesterol.

Example 7

The Reagent Composition A and the Reagent Composition B were prepared in the following way:

Reagent Composition A

| | |
|---|---|
| PIPES buffer solution, pH 6.8 | 50 mmol/L |
| Cholesterol esterase [CEBP-M produced by ASAHI KASEI PHARMA] | 5 U/mL |
| Cholesterol oxidase | 2.5 U/mL |
| Sphingomyelinase [SPC produced by ASAHI KASEI PHARMA] | 2.5 U/mL |
| Catalase | 1000 U/mL |
| TOOS | 2.0 mmol/L |
| Emulgen A-60 (Trade Name) | 0.1% (w/v) |

Reagent Composition B

| | |
|---|---|
| PIPES buffer solution, pH 6.8 | 50 mmol/L |
| Cholesterol esterase [CHE-2 produced by AMANO ENZYME] | 4 U/mL |
| 4-Aminoantipyrine | 4.0 mmol/L |
| Peroxidase | 20 units/mL |
| Sodium azide | 0.05% (w/v) |
| Emulgen 709 (Trade Name) | 0.1% (w/v) |

The measurement was carried out in the same manner as in Example 1, and the measurement result was compared with the value obtained by using RLP-cholesterol "JIMRO" II (Trade Name). The result is shown in FIG. 7.

Figure 7:
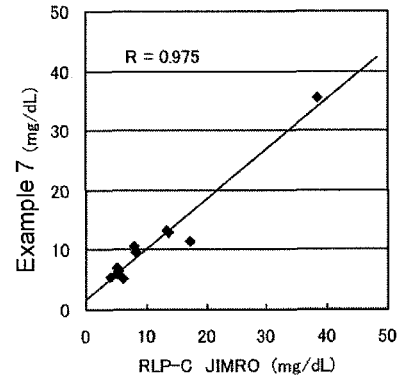
FIG. 7 shows the correlation between the quantification results of cholesterol in RLP by the method of the present invention described in Example 7 below and the quantification results by a known method using anti-RLP monoclonal antibody.

As shown in FIG. 7, a good correlation was observed between the method of this Example and the method using RLP-cholesterol "JIMRO" II (Trade Name) which is a reagent for measuring RLP cholesterol.

The invention claimed is:

1. A method for quantifying remnant-like lipoprotein cholesterol in a sample containing different lipoproteins including the remnant-like lipoprotein, said method comprising:

step (1) decomposing cholesterol in lipoproteins in the sample except for cholesterol in the remnant-like lipoprotein by decomposing the cholesterol to make it undetectable in step (2); and step (2) quantifying cholesterol in the remaining remnant-like lipoprotein, wherein said step (1) is carried out under an action of a cholesterol esterase having a molecular weight of more than 40 kDa and not having a subunit having a molecular weight of 40 kDa or less; and said step (2) is carried out under an action of a cholesterol esterase having a molecular weight of 40 kDa or less or a cholesterol esterase having a subunit having a molecular weight of 40 kDa or less.

2. The method according to claim 1, wherein said step (1) further comprises treating said sample with said cholesterol esterase and a cholesterol oxidase, and removing generated hydrogen peroxide of step (1); and said step (2) further comprises treating said sample with said cholesterol esterase and cholesterol oxidase, and quantifying generated hydrogen peroxide of step (2).

3. The method according to claim 1 or 2, wherein said step (1) and said step (2) are carried out in the presence of a nonionic surfactant.

4. The method according to claim 1, wherein a nonionic surfactant is used in said step (1) and said step (2), and wherein said nonionic surfactant comprises at least one selected from the group consisting of a polyoxyethylene derivative having an HLB value of 11 to 13, polyoxyethylene alkyl ether, polyoxyalkylene alkyl ether and polyoxyethylene alkyl phenyl ether.

5. The method according to claim 1, wherein said step (1) further comprises treating said sample with a phospholipase.

* * * * *